(12) United States Patent
Masters et al.

(10) Patent No.: US 8,178,483 B2
(45) Date of Patent: May 15, 2012

(54) POLYMERIC ENCAPSULATES HAVING A QUATERNARY AMMONIUM SALT AND METHODS FOR PRODUCING THE SAME

(75) Inventors: James G. Masters, Ringoes, NJ (US); Shira Pilch, Highland Park, NJ (US)

(73) Assignee: Colgate-Palmolive Company, New York, NY (US)

(*) Notice: Subject to any disclaimer, the term of this patent is extended or adjusted under 35 U.S.C. 154(b) by 733 days.

(21) Appl. No.: 11/694,032

(22) Filed: Mar. 30, 2007

(65) Prior Publication Data

US 2008/0242767 A1  Oct. 2, 2008

(51) Int. Cl.
*C11D 3/48* (2006.01)
*C11D 3/37* (2006.01)

(52) U.S. Cl. ........ 510/384; 510/349; 510/382; 510/441; 510/500; 510/504; 424/49; 424/53; 424/490; 424/497

(58) Field of Classification Search ............... 510/349, 510/382, 384, 441, 500, 504; 424/490, 497, 424/49, 53
See application file for complete search history.

(56) References Cited

U.S. PATENT DOCUMENTS

| | | |
|---|---|---|
| 3,538,230 A | 11/1970 | Pader et al. |
| 3,689,637 A | 9/1972 | Pader |
| 3,711,604 A | 1/1973 | Colodney et al. |
| 3,911,104 A | 10/1975 | Harrison |
| 3,935,306 A | 1/1976 | Roberts et al. |
| 3,962,463 A * | 6/1976 | Witzel ............... 426/5 |
| 3,994,827 A * | 11/1976 | Sakai et al. ........... 428/402.22 |
| 4,040,858 A | 8/1977 | Wason |
| 4,255,413 A * | 3/1981 | Rattie et al. ........... 424/452 |
| 5,132,117 A * | 7/1992 | Speaker et al. ........... 424/490 |
| 5,300,305 A * | 4/1994 | Stapler et al. ........... 424/490 |
| 5,326,484 A | 7/1994 | Nakashima et al. |
| 5,484,584 A * | 1/1996 | Wallace et al. ........... 424/1.29 |
| 5,733,572 A * | 3/1998 | Unger et al. ........... 424/450 |
| 5,753,264 A * | 5/1998 | Magdassi et al. ........... 424/451 |
| 5,935,553 A * | 8/1999 | Unger et al. ........... 424/9.51 |
| 6,007,795 A * | 12/1999 | Masterman et al. ........... 424/49 |
| 6,207,197 B1 | 3/2001 | Illum et al. |
| 6,514,933 B1 * | 2/2003 | Young et al. ........... 512/1 |
| 6,589,511 B1 * | 7/2003 | Shimizu ........... 424/49 |
| 6,589,562 B1 | 7/2003 | Shefer et al. |
| 6,743,444 B2 | 6/2004 | Jones et al. |
| 6,790,460 B2 | 9/2004 | Shefer et al. |
| 6,884,432 B2 | 4/2005 | Yaszemski et al. |
| 7,018,651 B2 | 3/2006 | Burger et al. |
| 7,053,034 B2 | 5/2006 | Shefer et al. |
| 7,157,102 B1 * | 1/2007 | Nuwayser ........... 424/490 |
| 7,749,332 B2 * | 7/2010 | Jonke et al. ........... 134/25.2 |
| 2003/0004449 A1 * | 1/2003 | Lafratta et al. ........... 602/48 |
| 2003/0035981 A1 * | 2/2003 | Capps ........... 428/703 |
| 2004/0013723 A1 * | 1/2004 | Parikh et al. ........... 424/456 |
| 2005/0260266 A1 * | 11/2005 | Gebreselassie et al. ........... 424/468 |
| 2006/0035854 A1 * | 2/2006 | Goldstein et al. ........... 514/44 |
| 2006/0134011 A1 * | 6/2006 | Shanahan ........... 424/49 |
| 2007/0148459 A1 * | 6/2007 | Joseph et al. ........... 428/402.2 |
| 2007/0197418 A1 * | 8/2007 | Rahse ........... 510/407 |
| 2007/0202315 A1 * | 8/2007 | Duffield et al. ........... 428/304.4 |
| 2008/0118734 A1 * | 5/2008 | Goodwin et al. ........... 428/221 |
| 2008/0152677 A1 * | 6/2008 | Colle et al. ........... 424/401 |
| 2008/0175910 A1 * | 7/2008 | Andre et al. ........... 424/472 |
| 2008/0175918 A1 * | 7/2008 | Laulicht ........... 424/490 |
| 2008/0274148 A1 * | 11/2008 | Creeth ........... 424/401 |
| 2009/0252809 A1 * | 10/2009 | Galeone et al. ........... 424/497 |
| 2010/0028433 A1 * | 2/2010 | Baker et al. ........... 424/484 |

FOREIGN PATENT DOCUMENTS

| | | |
|---|---|---|
| EP | 0 108 565 | 5/1984 |
| EP | 0478326 | 4/1992 |
| EP | 0528466 | 2/1993 |
| EP | 1184029 * | 3/2002 |
| EP | 1184029 A1 | 6/2002 |
| EP | 1393706 | 3/2004 |
| JP | 2003104871 A | 4/2003 |
| JP | 2004237177 A | 8/2004 |
| JP | 2005097291 A | 4/2005 |
| WO | 01/07000 * | 2/2001 |
| WO | 0107000 A1 | 2/2001 |
| WO | WO 02/074430 | 9/2002 |
| WO | WO 03/024415 | 3/2003 |
| WO | WO 03/106809 A1 | 12/2003 |
| WO | 2004/011011 * | 2/2004 |
| WO | 2004011011 A1 | 2/2004 |
| WO | 2004021798 A1 | 3/2004 |

OTHER PUBLICATIONS

International Search Report dated Jun. 30, 2008.

* cited by examiner

*Primary Examiner* — Charles Boyer

(74) *Attorney, Agent, or Firm* — Nikhil A. Heble

(57) ABSTRACT

A quaternary ammonium salt encapsulated by a polymeric microcapsule and methods for manufacturing such microcapsules are described. The quaternary ammonium salt can be cetylpyridinium chloride. The polymeric microcapsule encapsulating the quaternary ammonium salt can be used as an ingredient in a dentifrice.

14 Claims, 6 Drawing Sheets

Control

POLYMERIC ENCAPSULATES HAVING A QUATERNARY AMMONIUM SALT AND METHODS FOR PRODUCING THE SAME

BACKGROUND OF THE INVENTION

Polymeric microcapsules can be produced by one of several methods readily known in the art. Such methods include single and double emulsion solvent evaporation techniques.

Polymeric microcapsules have a wide variety of uses, such as use in drug delivery systems and personal care products, including dentifrices (i.e., a substance, such as a paste or powder, for cleaning the teeth). However, polymeric microcapsules generally do not provide good protection of an active ingredient encapsulated by the microcapsule from its external environment, such as one composed of a dentifrice formulation, while providing extended release of the active ingredient.

Cetylpyridinium chloride (CPC) is a cationic, surfactant-like, broad-spectrum antimicrobial agent that can be used for oral-care applications. However, due to its positive charge, CPC forms stable complexes with various common ingredients often used in, for example, dentifrices, such as sodium lauryl sulfate (SLS), an anionic surfactant. These types of reactions preclude the use of CPC in for example, common dentifrice formulations to deliver effective antimicrobial benefits.

In dentifrice applications, in order for microcapsules to stay intact during the toothpaste making and storage process, the microcapsules should possess the following properties: 1) good mechanical properties to sustain shear forces up to about 1000/s during mixing and high speed filling; 2) good temperature stability that allow the capsules to stay intact at temperatures up to about 71° C.; 3) good chemical stability that allows the capsules to be stable in the presence of sodium lauryl sulfate having a concentration of up to about 2% and a pH of about 5-8, and various water and humectants ratios. In addition, upon brushing, the microcapsules should break and release CPC to the oral cavity directly without formation of inactive complexes.

There are a number of triggers that allow the breakage of microcapsules during brushing, such as: 1) a mechanical trigger due to the grinding and shearing of toothbrush bristles; 2) a pH trigger due to the change in pH from a dentifrice base to an oral cavity environment; 3) an osmotic trigger due to the dilution of a dentifrice by saliva in the mouth during teeth brushing; and 4) an enzymatic trigger due to the breakage of polymer bonds by enzymes in the mouth.

It has also recently been recently reported in the literature that polymer microcapsules having mucoadhesive polymers has been formed via a water-in-oil emulsion method.

Accordingly, there is still a need for polymeric microcapsules that provide good protection of the active ingredient from its external environment while providing extended release profiles of the active ingredient over a significant period of time, such as a 24 hour time period. In addition, such polymeric microcapsules used in dentifrices, should have mucoadhesive properties that allow for extended release profiles of the active ingredient over a significant time period. In particular, there is still a need for an encapsulation technology to shield active ingredients, such as CPC, from incompatible ingredients, such as SLS.

BRIEF SUMMARY OF THE INVENTION

The present invention further provides for a process for manufacturing an antimicrobial dentifrice that comprises (a) encapsulating quaternary ammonium salt within a polymeric microcapsule, and (b) admixing a dentifrice with the encapsulated quaternary ammonium salt.

Another aspect of the present invention is a method of producing quaternary ammonium salt encapsulated by a polymeric microcapsule having an average diameter of about 5 microns to about 50 microns, comprising (a) dissolving the quaternary ammonium salt in an aqueous phase, (b) dispersing the aqueous phase within a hydrophobic organic solvent having a dissolved polymer to form a solution, (c) dispersing the solution in an external aqueous phase, and (d) removing the solvent from the external aqueous phase of step (c) to form quaternary ammonium salt encapsulated polymeric microcapsules.

A further aspect of the present invention includes a method of producing quaternary ammonium salt encapsulated by a polymeric microcapsule having an average diameter of about 5 microns to about 50 microns comprising (a) dissolving a polymer and the quaternary ammonium salt in an aqueous phase, (b) dispersing the aqueous phase as water-in-oil emulsion drops, and (c) stirring the emulsion of step (b) at elevated temperatures to evaporate the aqueous phase and form quaternary ammonium salt encapsulated polymeric microcapsules.

BRIEF DESCRIPTION OF THE DRAWINGS

The foregoing summary, as well as the following detailed description of the embodiments of the invention, will be better understood when read in conjunction with the appended drawings. It should be understood, however, that the invention is not limited to the precise arrangements and instrumentalities shown. In the drawings.

DETAILED DESCRIPTION OF THE INVENTION

The present invention provides for a composition that includes a quaternary ammonium salt encapsulated within a polymeric microcapsule. The composition can optionally include various active agents as well. The active agents can be a stannous ion agent, triclosan, triclosan monophosphate, chlorhexidine, alexidine, hexetidine, sanguinarine, benzalkonium chloride, salicylanilide, arginate esters, ethyl lauryl arginate, bisphenols, domiphen bromide, tetradecylpyridinium chloride (TPC), N-tetradecyl-4-ethylpyridinium chloride (TDEPC), octenidine, delmopinol, octapinol, nisin, zinc ion agent, copper ion agent, essential oils, furanones, bacteriocins, salts thereof, mixtures thereof, and similar known actives.

The quaternary ammonium salt of the present embodiment may be cetylpyridinium chloride. In addition, more than one quaternary ammonium salt may be encapsulated in a single polymeric microcapsule.

The polymeric microcapsules of the present invention can include a variety of standard microcapsule materials. Such microcapsule materials, without limitation, are chitin, chitosan, polycaprolactone, polyacrylic acid, and their derivatives and copolymers. In particular, chitosan may have an advantage that it shows pH dependent behavior near physiological pH, with increased solubility at lower pH. Thus, it may be possible to take advantage of this property in dentifrice formulation as the rate of CPC diffusion out of a polymeric microcapsule will be slower at pH of about 8-9 than at about 7.

The use of the term "polymeric," as used herein to describe polymeric microcapsules, means that at least one of the ingredients forming the microcapsule is a polymeric material, but it should be understood that other ingredients may be used as well in forming the microcapsule which are non-polymeric substances, such as gums, gelatin, etc.

The polymeric microcapsules can have a diameter of about 5 microns to about 50 microns, the size being more or less if usage is consistent with the size variation.

The composition can also include an optional fluoride ion source. A fluoride ion source is considered anything that can release a fluoride ion in an aqueous environment. Examples of such fluoride ion sources are described in U.S. Pat. Nos. 3,538,230; 3,689,637; 3,711,604; 3,911,104; 3,935,306; and 4,040,858, which are all incorporated by reference in relevant part. However, it should be understood that any suitable fluoride ion source known in the art or to be developed can be provided to the composition.

A second aspect of the present invention provides for a method of producing polymeric microcapsules encapsulating a quaternary ammonium salt. This method includes (a) dissolving a quaternary ammonium salt (as noted above) in an aqueous phase, such as MilliQ water or distilled water, (b) dispersing the aqueous phase within a hydrophobic organic solvent, having a dissolved polymer (such as chitin, chitosan, polycaprolactone, or polyacrylic acid) to form a solution, (c) dispersing the solution in an external aqueous phase (i.e., a second aqueous phase), and (d) removing the solvent from the external aqueous phase of step (c), for example by evaporation or any other method known in the art.

The invention may also provide a method of producing a quaternary ammonium salt encapsulated by a polymeric microcapsule having a microcapsule diameter of about 5 microns to about 50 microns. This method includes (a) dissolving a polymer (as described above) and a quaternary ammonium salt (as described above) in an aqueous phase, (b) dispersing the aqueous phase as water-in-oil emulsion drops (for example by pipetting), and (c) stirring the emulsion of step (b) at an elevated temperature to evaporate the aqueous phase thus forming quaternary ammonium salt encapsulated polymeric microcapsules.

The elevated temperature of this method is preferably about 95° C. to about 100° C.

The quaternary ammonium salt of this method can be any quaternary ammonium salt described above and preferably cetylpyridinium chloride.

The polymeric microcapsules produced according to this method can be made in various shapes and forms such as a microsphere, microparticle, and the like.

Also included in the invention is a process for manufacturing an antimicrobial dentifrice. The dentifrice can be, without limitation, a paste, gel, powder, etc. The process includes encapsulating quaternary ammonium salt, such as those described herein, within polymeric microcapsules using the methods of this disclosure, and admixing a dentifrice with the encapsulated quaternary ammonium salt.

The quaternary ammonium salt of this process is preferably cetylpyridinium chloride.

Also included in the invention is a method of producing quaternary ammonium salt encapsulated by a polymeric microcapsule having an average diameter of about 5 microns to about 50 microns. This method includes (a) dissolving the quaternary ammonium salt in an aqueous phase (such as MilliQ water or distilled water) (b) dispersing the aqueous phase within a hydrophobic organic solvent (as described above) having a dissolved polymer (e.g., chitin, chitosan, polycaprolactone, or polyacrylic acid) to form a solution, (c) dispersing the solution in an external aqueous phase, and (d) removing the solvent from the external aqueous phase (for example by evaporation) thus forming quaternary ammonium salt encapsulated polymeric microcapsules.

Also included in the invention is a personal care product that includes quaternary ammonium salt encapsulated polymeric microcapsules. The personal care product can further include a fluoride ion source. Such personal care products are for example toothpastes, mouthwashes, mousses, sprays, films, and other portable forms.

The present invention can produce microcapsules having the following properties: 1) a microcapsule size ranging from nanometers to millimeters (generally smaller the microcapsule size, the better the mechanical stability); 2) a size distribution; 3) a microcapsule shell thickness ranging from nanometers to micrometers; and 4) impermeability of the shell and/or a dual shell layer structure.

The present invention can also use cationic surfactant-like compounds, such as CPC, as an emulsion stabilizer to enhance encapsulation efficiency during the process of forming polymeric microcapsules. Such capsules can shield the CPC from other ingredients outside the polymeric microcapsules, such as those in a dentifrice, and as such can deliver the CPC as an effective antimicrobial agent upon the breakage of the capsules during teeth brushing.

Benefits of encapsulating CPC include preventing adverse interactions between CPC and a dentifrice formulation to maximize the delivery of effective CPC (i.e., CPC not in a stable complex form) and the CPC itself can act as an emulsion stabilizer to prevent the coalescence of water or oil droplets in water-in-oil or oil-in-water emulsions.

By way of example, and not limitation, specific embodiments of the present invention are illustrated in the following examples.

Example 1

Chitosan cetylpyridinium chloride (CPC) microcapsules having 180 mg of CPC (a composition of 10 wt % CPC (1% of the CPC was rhodamine-labeled)) were produced and evaluated as described below.

The following materials were used to prepare chitosan microcapsules from water-in-oil emulsions:
Chitosan (>85% deacetylated, Aldrich 417963),
MilliQ water,
Glacial acetic acid,
FD&C blue #1 food coloring dye,
Cetylpyridinium chloride (CPC),
Mineral oil (white, heavy), and
Sorbitan monooleate (Span-80) surfactant.

A chitosan solution was prepared by mixing 9 grams of chitosan with 600 ml of water/1% (vol.) acetic acid solution. The chitosan was dissolved in the 600 ml of water/1% (vol.) acetic acid solution by stirring and heating the mixture to approximately 60° C. for about 1 day. Then 3.3 ml of aqueous solution containing 10 wt % CPC and 10 mg blue dye (pre-dissolved) was added to 200 ml of the chitosan solution.

A mixture was then prepared by adding an emulsifier (IKA RE162/P) with 800 ml of mineral oil and 8 ml of Span-80, and stirred at 100 rpm for 5 minutes to mix. The mixture was allowed to sit for 20 minutes to allow air bubbles to rise and pop. The chitosan solution was then added to the mixture through two 60 ml syringes with 16 gauge needles over a period of approximately 20 minutes. The resulting emulsion was then stirred for another 30 minutes after adding the last of the chitosan solution.

The emulsion was then transferred to a 2 L Pyrex beaker on a magnetic stir plate. The emulsion was heated to approximately 70° C. while stirring and left overnight (approximately 14-16 hours) to evaporate the acetic acid and most of the water. The emulsion changed from very milky, light blue to a cloudy, darker blue color. The emulsion was then heated to approximately 95°-100° C. with continued stirring until the following day (approximately 24 hours). The color of the emulsion shifted from blue to pale green.

The emulsion was then collected into 50 ml centrifuge tubes and spun each at 3,500 rpm for 10 minutes. Most of the particles had settled following centrifugation, but a large fraction of the smallest particles (having a size of a few microns or less) remained suspended. The solution was decanted into waste. Under the microscope it was apparent that centrifuged particles were quite densely packed and even somewhat deformed, indicating there was likely still some residual water keeping the particles soft.

In half of the centrifuge tubes, particles were re-suspended in the small, remaining amount of mineral oil using a glass pipette. All of the remaining particle/oil slurry was transferred from these tubes to a glass vial (total volume approximately 15 ml), and centrifuged again at 3,500 rpm for 1 hour. The solution was again decanted into waste and residual oil was removed with a pipette as far as possible.

In the other half of the tubes, particles were resuspended in approximately 10 ml hexane in each tube by vortexing. Liquid was collected from all tubes into 2 tubes, which were then centrifuged at 3,500 rpm for 10 minutes. Solution was decanted into waste and particles were resuspended in approximately 10 ml hexane in each tube. Finally, the solution was filtered through qualitative filter paper by gravity filtration and left to dry in a fume hood.

Methods—Physical and Chemical Stability Characterization: Physical characterization of chitosan, CPC-encapsulated microcapsules was conducted by a mechanical stability evaluation. Chemical characterization of chitosan, CPC-encapsulated microcapsules was conducted by: 1) a hydration experiment and 2) a chemical stability in the presence of SLS experiment.

Mechanical Stability Characterization: The mechanical stability of chitosan, CPC-encapsulated microcapsules were evaluated under continual shearing conditions at various shear strengths of 100/s and 500/s.

Chemical Stability Characterization:

Hydration Experiment: Microscopic techniques were used to evaluate chitosan, CPC-encapsulated microcapsules in water at various pH conditions. Fluorescent spectroscopic techniques were used to evaluate the fluorescence change in the supernatant portion of the chitosan, CPC-encapsulated microcapsules in suspension.

Stability in the Presence of SLS Experiment: Chitosan, CPC-encapsulated microcapsules were suspended in 1% SLS and evaluated for interaction with SLS.

Results: The chitosan, CPC-encapsulated microcapsules produced according to this method were quite stable and allowed for the rapid release of CPC, due to the hydrophilicity of the polymer matrix. In addition, it was found that the addition of 10 wt % CPC to the aqueous phase eased processing by allowing the formation of smaller emulsion droplets at a given shear rate.

Figure 1A:
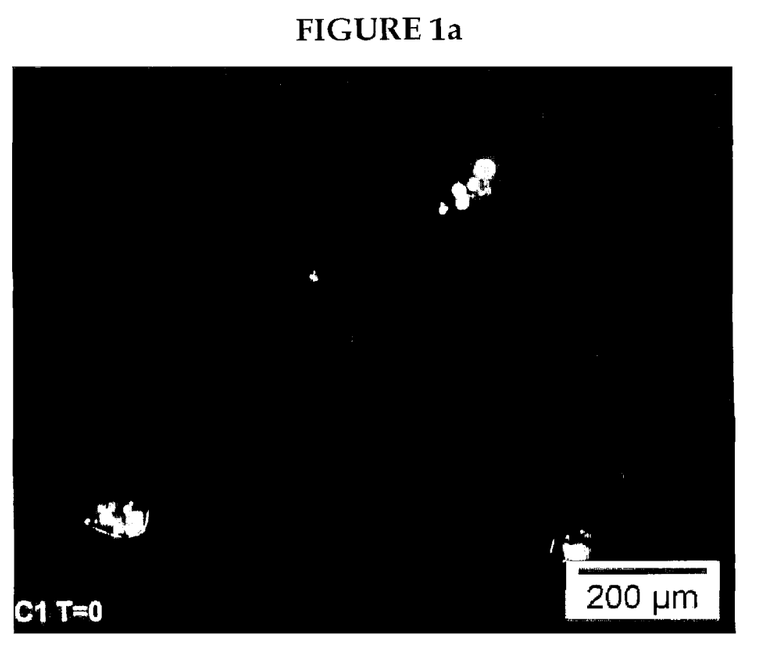
FIG. 1a is a fluorescent image of chitosan microcapsules in water at a pH of 7 at time=0.
Figure 1B:
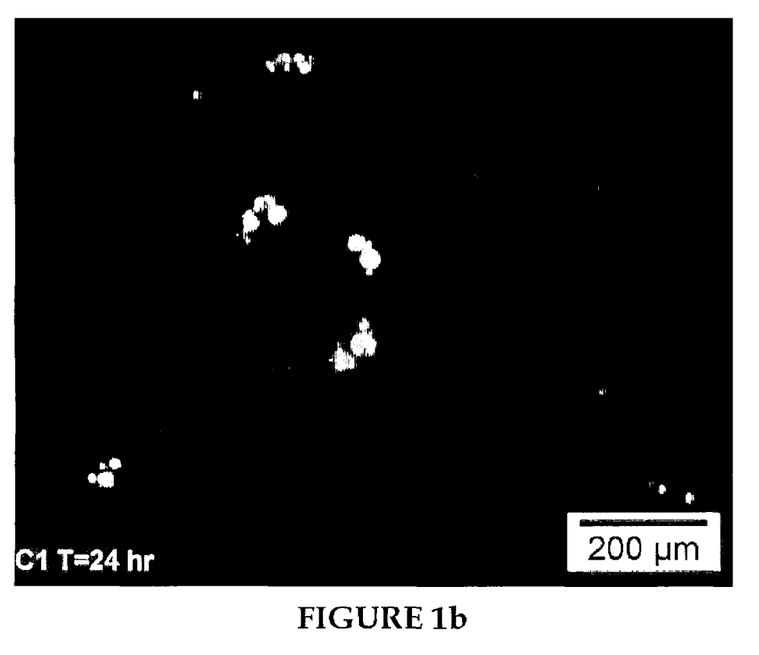
FIG. 1b is a fluorescent image of chitosan microcapsules in water at a pH of 7 at time=24 hours.

A fluorescence image of a collection of chitosan microcapsules is shown in FIGS. 1a and 1b. The fluorescence derives from octadecyl rhodamine-B, which was incorporated at 1% of the concentration of CPC to serve as a tracer. FIG. 1a shows chitosan microcapsules at zero time. FIG. 1b shows the chitosan microcapsules at 24 hours time. There is little change in the shape and size of the chitosan microcapsules observed up to 24 hours at a pH of 7. In addition, the amount of rhodamine dye released from the chitosan microcapsules was characterized for up to 12 weeks at room temperature. Less than 0.1% of the rhodamine dye was released from the chitosan CPC encapsulated microcapsules.

Figure 2:
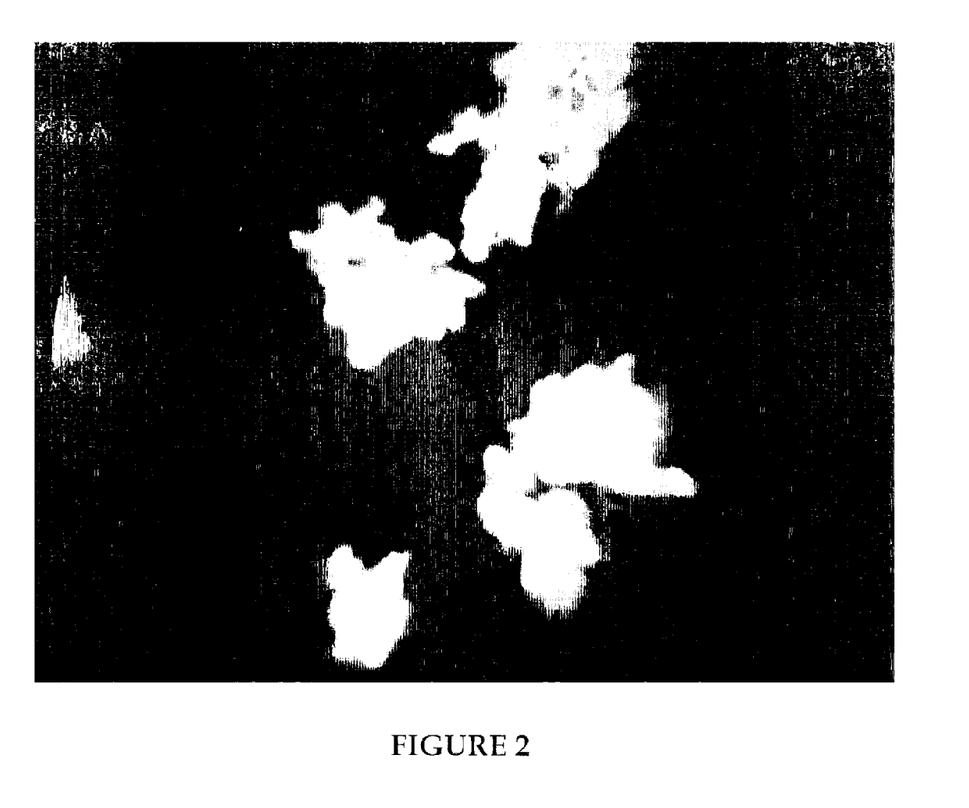
FIG. 2 is a fluorescent image of chitosan microcapsules in the presence of sodium lauryl sulfate.

FIG. 2 shows the chemical stability of chitosan CPC encapsulated microcapsules in the presence of 1% sodium lauryl sulfate (SLS). In 1% SLS, less than 0.1% of the chitosan microcapsules broke after 4 weeks time. In addition, no precipitation was observed due to SLS-CPC interaction.

Figure 3A:
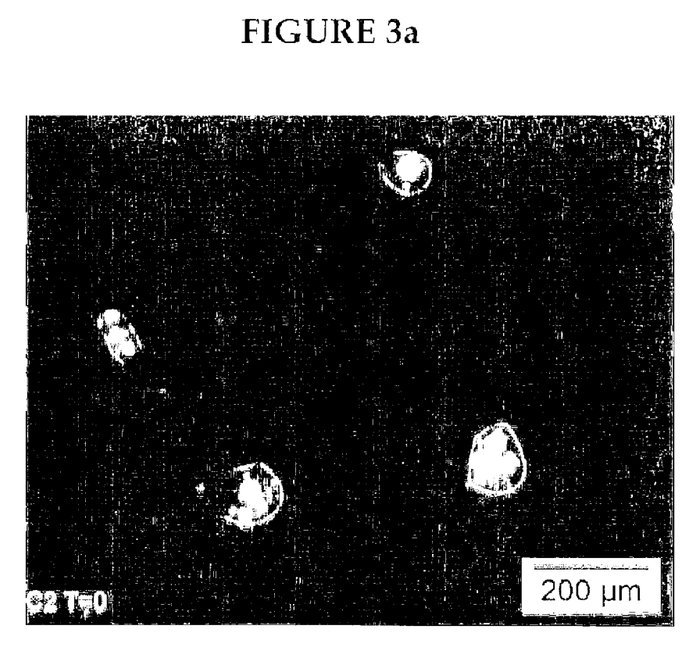
FIG. 3a is a fluorescent image of chitosan microcapsules in water at a pH of 4 at time=0.
Figure 3B:
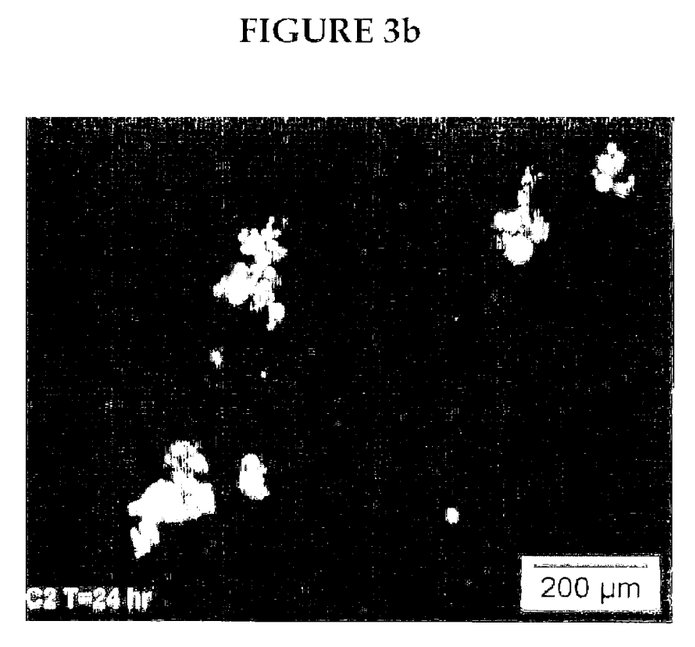
FIG. 3b is a fluorescent image of chitosan microcapsules in water at a pH of 4 at time=24 hours.
Figure 4A:
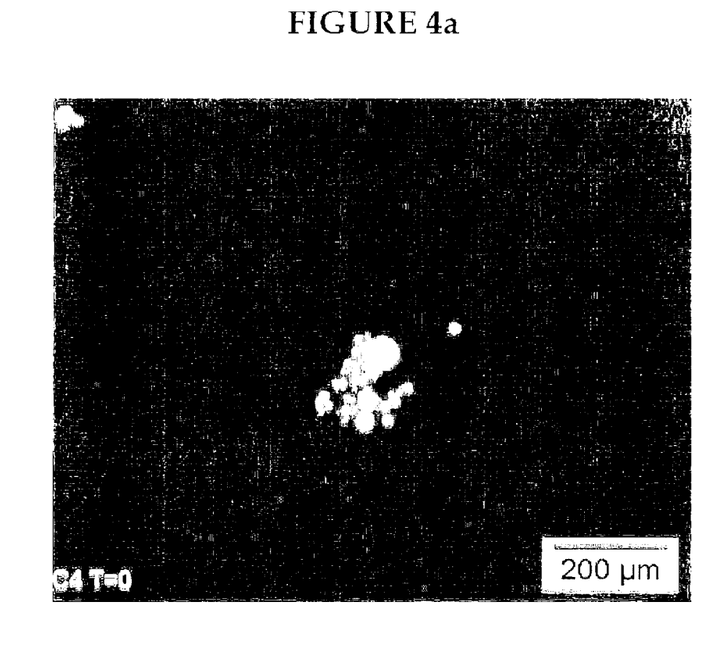
FIG. 4a is a fluorescent image of chitosan microcapsules in water at a pH of 9 at time=0.
Figure 4B:
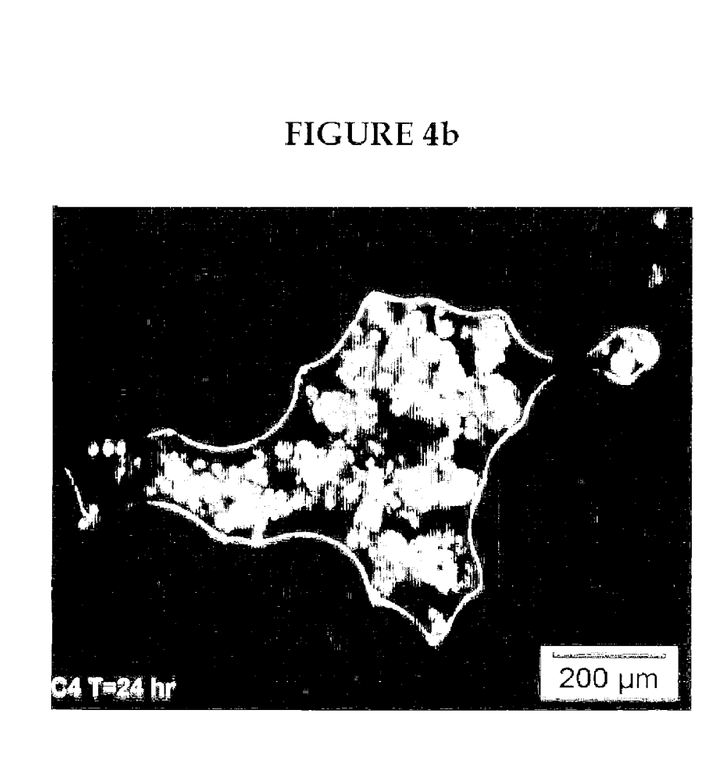
FIG. 4b is a fluorescent image of chitosan microcapsules in water at a pH of 9 at time=24 hours.

FIGS. 3 and 4 show the chemical stability of chitosan, CPC-encapsulated microcapsules at acidic and basic pH conditions. FIG. 3 shows the chitosan microcapsules to be stable in an aqueous environment for up to 24 hours at a pH of 4. FIG. 4 shows the chitosan microcapsules to be stable in an aqueous environment for up to 24 hours at a pH of 9.

Figure 5A:
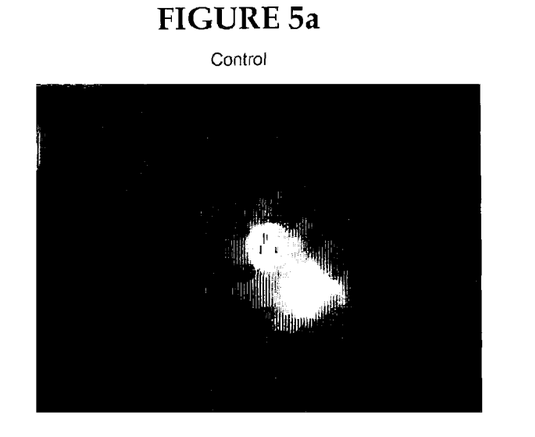
FIGS. 5a through 5c are fluorescent images of chitosan microcapsules in water at shear rates of 0/s, 100/s, and 500/s respectively.
Figure 5B:
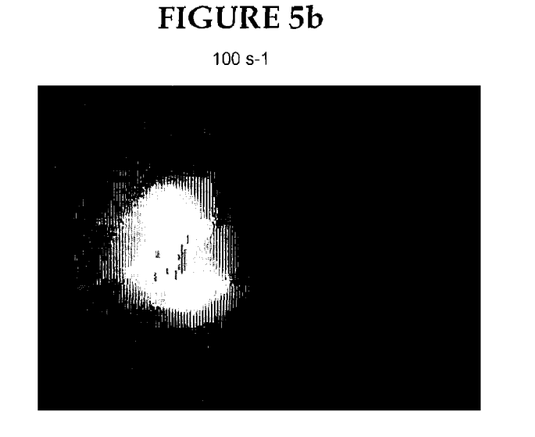
Figure 5C:
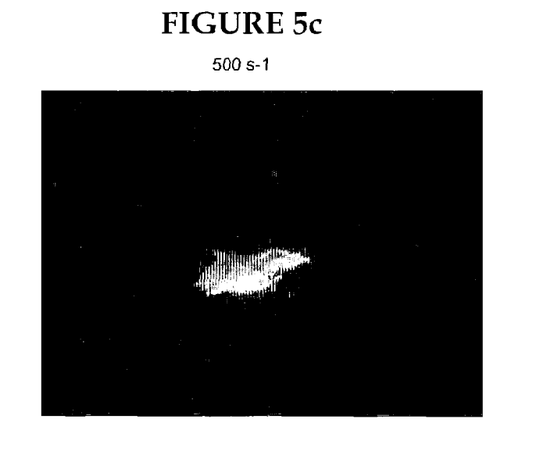

FIGS. 5a-5c show the mechanical stability of chitosan, CPC-encapsulated microcapsules at various shear rates. FIG. 5a shows chitosan microcapsules exposed to a shear rate of 0/s (that is, no shear) i.e., the control. FIG. 5b shows chitosan microcapsules exposed to a shear rate of 100/s. FIG. 5c shows chitosan microcapsules exposed to a shear rate of 500/s and in a state of active release of CPC.

Figure 6A:
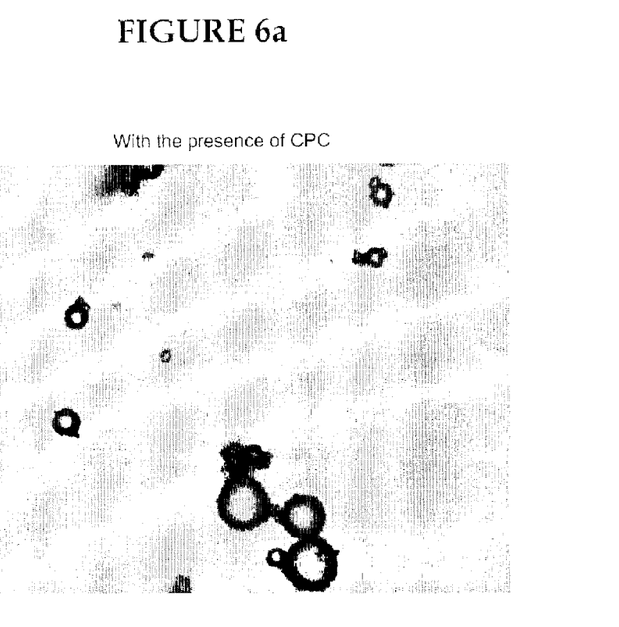
FIG. 6a is a fluorescent image of polymer microcapsules within the presence of cetylpyridinium chloride.
Figure 6B:
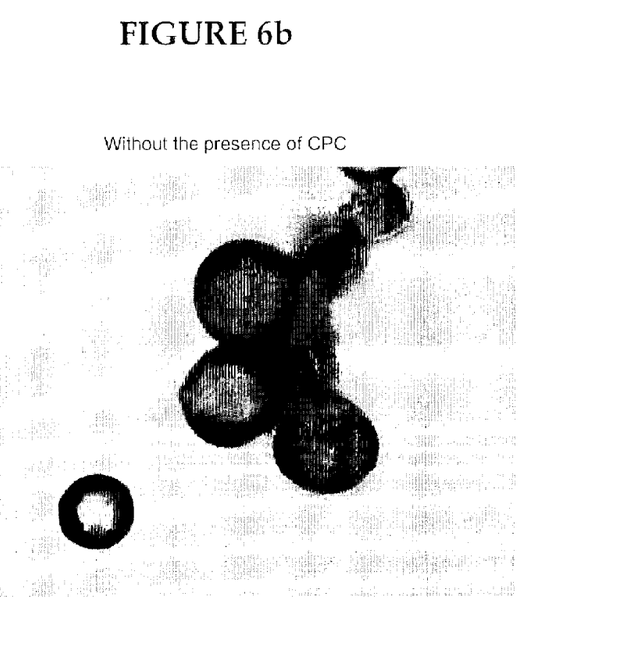
FIG. 6b is a fluorescent image of polymer microcapsules without the presence of cetylpyridinium chloride.

FIGS. 6a and 6b show the size of polymer microcapsules made with and without CPC. FIG. 6a shows the size of polymer microcapsules made with FD&C blue #1 alone and without CPC. FIG. 6b shows the size of polymer microcapsules made with FD&C blue #1 and CPC. When CPC is added to the emulsion, it prevents the coalescence of water droplets, which subsequently results in smaller capsules.

Thus, besides providing simpler processing, this method offers the advantage that a variety of water-soluble, biocompatible, and even mucoadhesive polymers can potentially be used.

Example 2

Examples of various dentifrice formulations are further illustrative of the present invention and are not intended to limit the invention in any way. Such formulations were made with CPC-encapsulated microcapsules produced in accordance with the present invention.

Table 1 provides a dentifrice composition with phosphate salts. Table 2 provides a dentifrice composition with Gantrez copolymer. Table 3 provides a dentifrice composition with PCC. Table 4 provides a dentifrice composition using a liquid formulation.

TABLE 1

| Ingredients | % Wt/Wt |
| --- | --- |
| Water | 18.46 |
| NaF | 0.24 |
| Na Saccharin | 0.45 |

TABLE 1-continued

| Ingredients | % Wt/Wt |
| --- | --- |
| Sorbitol | 28 |
| Glycerine | 12 |
| Gantrez-97 | 1 |
| NaOH (50% solution) | 2 |
| Tetrasodium pyrophosphate | 1 |
| Sodium Tripolyphosphate | 7 |
| Carrageenan | 0.35 |
| Carboxymethylcellulose (CMC) | 0.8 |
| Silica | 25 |
| Sodium Lauryl Sulfate (SLS) | 1.2 |
| Flavor | 1.0 |
| CPC Microcapsules | 1.5 |

TABLE 2

| Ingredients | % Wt/Wt |
| --- | --- |
| Water | 27.26 |
| NaF | 0.24 |
| Na Saccharin | 0.3 |
| TiO$_2$ | 0.5 |
| Sorbitol | 21 |
| Glycerine | 20 |
| Polyethylene Glycol (PEG) | 0.5 |
| Gantrez-97 | 2 |
| NaOH (50% solution) | 1.2 |
| Carrageenan | 0.4 |
| Carboxymethylcellulose (CMC) | 1.1 |
| Silica | 21.5 |
| Sodium Lauryl Sulfate (SLS) | 1.5 |
| Flavor | 1.0 |
| CPC Microcapsules | 1.5 |

TABLE 3

| Ingredients | % Wt/Wt |
| --- | --- |
| Water | 31.89 |
| Monofluoride phosphate | 0.76 |
| Na Saccharin | 0.35 |
| Sorbitol | 21 |
| NaOH (50% solution) | 0.5 |
| Soda Ash | 0.75 |
| Xanthan | 0.2 |
| Carboxymethylcellulose (CMC) | 0.65 |
| Carrageenan | 0.2 |
| PCC | 29.4 |
| Silica | 10 |
| Sodium Lauryl Sulfate (SLS) | 1.6 |
| Flavor | 1.2 |
| CPC Microcapsules | 1.5 |

TABLE 4

| Ingredients | % Wt/Wt |
| --- | --- |
| Water | 4.68 |
| NaF | 0.26 |
| Na Saccharin | 0.37 |
| Sorbitol | 67.1 |
| Glycerine | 7.46 |
| Polyethylene GlycolPEG 600 | 1.5 |
| Tetrasodium pyrophosphate (TSPP) | 0.53 |
| Carrageenan | 0.23 |
| Carboxymethylcellulose (CMC) | 0.8 |
| Silica | 12.5 |
| Sodium Lauryl Sulfate (SLS | 1.6 |
| Coco Betaine | 0.37 |
| Flavor | 1.1 |
| CPC Microcapsules | 1.5 |

We claim:

1. An oral care composition comprising cetylpyridinium chloride encapsulated by polymeric microcapsules having an average diameter of 5 to 50 microns, wherein the polymeric microcapsules comprises chitosan.

2. The composition of claim 1, further comprising an active agent selected from the group consisting of stannous ion agent, triclosan, triclosan monophosphate, chlorhexidine, alexidine, hexetidine, sanguinarine, benzalkonium chloride, salicylanilide, arginate esters, ethyl lauryl arginate, bisphenols, domiphen bromide, tetradecylpyridinium chloride (TPC), N-tetradecyl-4-ethylpyridinium chloride (TDEPC), octenidine, delmopinol, octapinol, nisin, zinc ion agent, copper ion agent, essential oils, furanones, bacteriocins and salts thereof.

3. The composition of claim 1, wherein the composition further comprises a fluoride ion source.

4. A process for manufacturing an antimicrobial dentifrice comprising:
    encapsulating cetylpyridinium chloride within polymeric microcapsules; and
    admixing a dentifrice with the encapsulated cetylpyridinium chloride;
    wherein the polymeric microcapsules have an average diameter of 5 microns to 50 microns and comprise chitosan.

5. The process of claim 4, further comprising admixing a fluoride ion source with the dentifrice.

6. A method of producing cetylpyridinium chloride encapsulated by polymeric microcapsules having an average diameter of about 5 microns to about 50 microns, comprising:
    (a) dissolving the cetylpyridinium chloride in an aqueous phase;
    (b) dispersing the aqueous phase within a hydrophobic organic solvent having a dissolved polymer to form a solution;
    (c) dispersing the solution in an external aqueous phase; and
    (d) removing the solvent from the external aqueous phase of step (c) to form cetylpyridinium chloride encapsulated polymeric microcapsules;
    wherein the polymeric microcapsules comprise chitosan.

7. A personal care product comprising cetylpyridinium chloride encapsulated by a polymeric microcapsule produced according to claim 6.

8. The personal care product of claim 7, further comprising a fluoride ion source.

9. A method of producing cetylpyridinium chloride encapsulated by a polymeric microcapsules having an average diameter of 5 microns to 50 microns, comprising:
    (a) dissolving a polymer and the quaternary ammonium salt in an aqueous phase;
    (b) dispersing the aqueous phase as water-in-oil emulsion drops; and
    (c) stirring the emulsion of step (b) at an elevated temperature to evaporate the aqueous phase and form cetylpyridinium chloride encapsulated polymeric microcapsules;
    wherein the polymeric microcapsules comprise chitosan.

10. The method of claim 9, wherein the elevated temperature is about 95° C. to about 100° C.

11. A personal care product comprising cetylpyridinium chloride encapsulated by a polymeric microcapsules produced according to claim 9.

12. The personal care product of claim 11, further comprising a fluoride ion source.

13. A polymeric microcapsule encapsulating cetylpyridinium chloride, wherein the polymeric microcapsules have a diameter of 5 to 50 microns and comprise chitosan.

14. The polymeric microcapsule of claim 13, further comprising an active agent selected from the group consisting of stannous ion agent, triclosan, triclosan monophosphate, chlorhexidine, alexidine, hexetidine, sanguinarine, benzalkonium chloride, salicylanilide, arginate esters, ethyllauryl arginate, bisphenols, domiphen bromide, tetradecylpyridinium chloride (TPC), N-tetradecyl-4-ethylpyridinium chloride (TDEPC), octenidine, delmopinol, octapinol, nisin, zinc ion agent, copper ion agent, essential oils, furanones, bacteriocins, salts thereof; and mixtures thereof.

* * * * *